US00PP35431P2

(12) United States Plant Patent
Olesen

(10) Patent No.: US PP35,431 P2
(45) Date of Patent: Oct. 24, 2023

(54) ROSE PLANT NAMED 'POULREN037'

(50) Latin Name: *Rosa hybrida*
Varietal Denomination: Poulren037

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 16 days.

(21) Appl. No.: 17/803,609

(22) Filed: Sep. 13, 2022

(30) Foreign Application Priority Data

Sep. 24, 2021 (QZ) ..... PBR 2021/2356

(51) Int. Cl.
*A01H 5/02* (2018.01)
*A01H 6/74* (2018.01)

(52) U.S. Cl.
USPC ..... Plt./137
CPC ..... *A01H 6/749* (2018.05)

(58) Field of Classification Search
USPC ..... Plt./137, 138, 130, 139, 107, 148
CPC ... A01H 5/02; A01H 5/00; A01H 6/74; A01H 6/749
See application file for complete search history.

(56) References Cited

PUBLICATIONS

Floraland 2020, retrieved on Feb. 23, 2023 at http://flora-land.ro/floraland/wp-content/uploads/2020/10/Floraland-Trandafir-si-clematis.pdf, pp. 1, 10-11. (Year: 2020).*
Poulsen Roser A/S retrieved on Feb. 23, 2023 at https://www.poulsenroser.dk/en/roses/ShowProduct/67606?productGroup=REN, 2 pp. (Year: 2023).*

* cited by examiner

*Primary Examiner* — June Hwu

(57) ABSTRACT

A new garden rose plant of the Hybrid Tea class which has abundant, deep pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulren037'.

This application claims priority to Plant Breeder's Rights Application Number 2021/2356, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren037', originated as a single seedling from the stated cross.

The new variety may be distinguished from its male pollen parent and female seed parent primarily by the following characteristics. The male pollen parent plant has yellow flowers while the new variety has deep pink flowers. The female seed parent plant grows to 45 cm in height in one season, while 'Poulren037' grows to 55 cm in height.

The objective of the hybridization of this rose variety was to create a new and distinct variety with unique qualities, such as:

1. Uniform and abundant deep pink flowers;
2. Vigorous, but compact growth when propagated on its own roots;
3. Exceptional disease resistance; and
4. Strong flower perfume.

This combination of qualities is not present in previously available commercial cultivars of this type, known to the inventor, and distinguish 'Poulren037' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren037' was selected in the spring of 2014 by the inventor as a single plant from the progeny of the aforementioned hybridization.

Asexual reproduction of 'Poulren037' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren037' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren037'.

Specifically illustrated in FIG. 1 of the drawings are open flowers at various stages of development viewed from above, flower petals detached revealing reproductive flower parts, flower buds at various stages of opening, and sepals detached.

Figure 1:
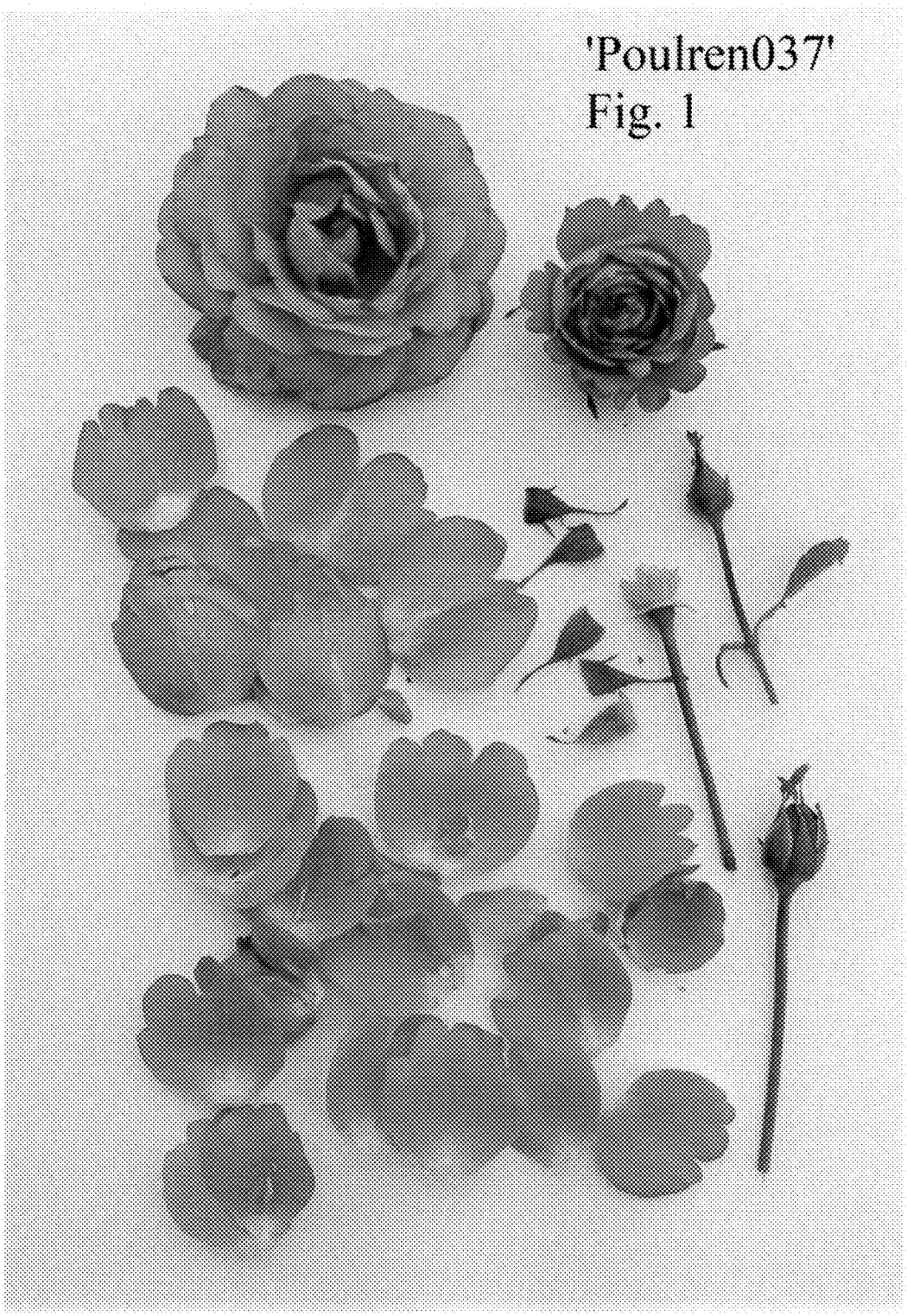
Figure 2:
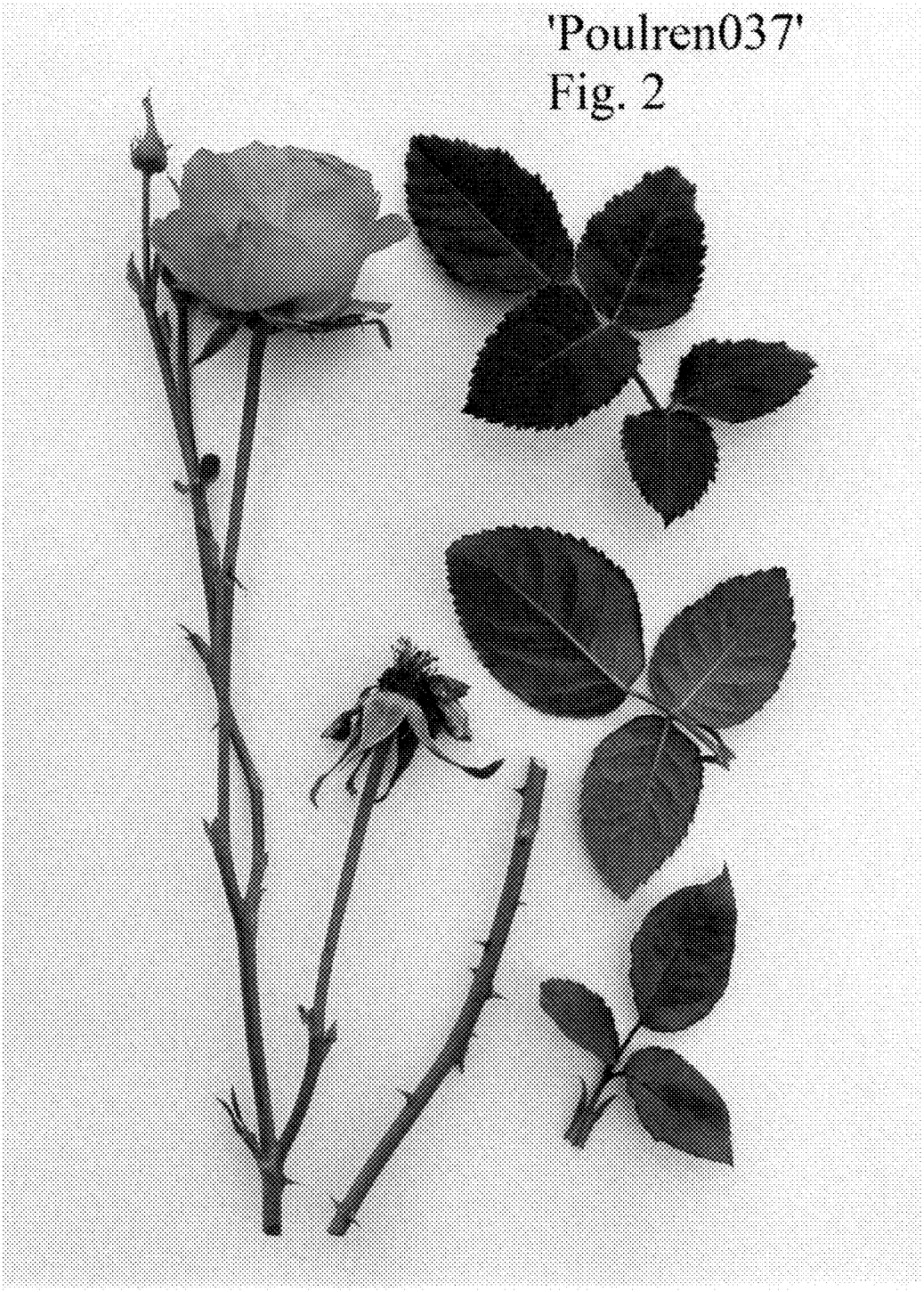

Specifically illustrated in FIG. 2 of the drawings are mature and juvenile leaves, and a flowering branch. Plants shown are 2 years of age.

DETAILED DESCRIPTION OF THE VARIETY

The following is a description of 'Poulren037', as observed in its growth in a field nursery in Linn County, Oregon. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren014', U.S. Plant Patent No. 26,569 are now compared to 'Poulren037'. While the comparison has a flower diameter of 90 mm, 'Poulren037' has a flower diameter of 100 mm. In terms of general tonality of open flowers the comparison variety is Red-Purple Group 67A with intonations of Red-Purple Group 71C, the claimed plant is Red-Purple Group N57B with intonations of Red Group 46B. While the claimed plant has 35 flower petals, 'Poulren014' has 90 petals.

Flower and Flower Bud

Blooming habit: Continuous.

Flower bud:

- *Size.*—Upon opening, 25 mm in length from base of receptacle to end of bud. Bud diameter is 13 mm.
- *Bud form.*—Urceolate.
- *Bud color.*—As sepals divide petals are Red Group 46A.
- *Sepal inner surface.*—Color: Yellow-Green Group 146D. Surface: Lightly pubescent.
- *Sepal outer surface.*—Color: Yellow-Green Group 144A with intonations of Greyed-Purple Group 183B. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—About 30 mm long, 12 mm wide.
- *Receptacle.*—Texture: Smooth. Size: 6 mm in height, 7 mm wide. Color: Yellow-Green Group 144A. Shape: Campanulate.
- *Pedicel.*—Surface: Smooth. Length: 40 to 80 mm. Diameter: 3 mm on average. Color: Yellow-Green Group 144B with intonations of Greyed-Red Group 178A. Strength: Strong.
- *Peduncle.*—Length: Variable between 5 to 30 mm. Diameter: About 3.5 mm. Color: Yellow-Green Group 144A. Texture: Smooth.

Flower bud development: Flower buds are borne in clusters of 3 flower buds per stem average. Development as a panicle.

Flower bloom:

- *Fragrance.*—Strong to moderate perfume.
- *Duration.*—The blooms have a duration on the plant of approximately 14 days. Petals fall cleanly away from plant after flowers have fully matured.
- *Size.*—Flower diameter is 100 mm when open. Flower depth is 48 mm.
- *Flower shape.*—Deep open cup, double flower, with petals that curve out from the center. Viewed from above the flower is round.
- *Shape of flower, side view.*—The upper portion is flat. The lower portion is flat.

Petalage: Under normal conditions, flowers have about 35 petals.

General tonality of flower: Open flowers are Red-Purple Group N57B with intonations of Red Group 46B. After flowers have been open for one week, the tonality is Red-Purple Group N57B.

Petal color:

- *Upon opening, outer and inner petals.*—Upper surface: Red-Purple Group N57A. At the basal zone Yellow Group 9A. Lower surface: Basal zone Red Group 41A. Middle and marginal zone Red-Purple Group 58B. Additional streaks of Yellow Group 8C.
- *Basal petal spots, upon opening.*—Upper surface: Medium sized Yellow Group 9A. Lower surface: Medium sized Yellow Group 4B and Yellow Group 7B.
- *After opening, outer petals.*—Upper surface: Red Group 45C with a basal zone of Yellow Group 6A. Streaks of Yellow Group 6A in the middle zone. Lower surface: Red Group 46C with streaks of Yellow Group 7C.
- *After opening, inner petals.*—Upper surface: Red Group 43C, and Red-Purple Group N57A. Basal zone Yellow Group 7A. Lower surface: Red Group 54A. Yellow Group 5C at the basal zone, and streaking outward.
- *Basal petal spots, after opening.*—Upper surface: Medium sized Yellow Group 7A Lower surface: Medium sized Yellow Group 7C or 5C.

Petals:

- *Petal reflex.*—Somewhat reflexed.
- *Margin.*—Many clefts in the margin. Strong undulations.
- *Shape.*—Broad and elliptic. Apex shape: Rounded. Base shape: Acute.
- *Size.*—45 mm (l) by 50 mm (w).
- *Texture.*—Smooth.
- *Thickness.*—Average.

Petaloids:

- *Size.*—30 mm (l) by 15 mm (w).
- *Quantity.*—About 6.
- *Shape.*—Elliptical with an acute base and rounded apices.
- *Color.*—On the upper surface Red Group 43C, and Red-Purple Group N57A. At the basal zone Yellow Group 7A. The lower surface is Red Group 54A, and Yellow Group 5C at the basal zone.

Reproductive flower parts:

- *Pollen.*—None observed.
- *Anthers.*—Size: 3 mm in length. Color: Yellow-Orange Group 14A. Quantity: 45 on average.
- *Filaments.*—Color: Yellow Group 11A. Length: 5 mm.
- *Pistils.*—Length: 10 mm. Quantity: 30 on average.
- *Stigmas.*—Color: Greyed-Yellow Group 160B.
- *Styles.*—Color: Green-White Group 157A with intonations of Red-Purple Group 58B.

*Location of stigmas.*—Superior in location relative to the length of the filaments and the height of the anthers.

*Hips.*—None Observed.

Plant

Plant growth: Upright. Plants are 55 cm in height, and 43 cm wide.

Stems:

*Color of juvenile growth.*—Yellow-Green Group 144A.

*Color of mature growth.*—Yellow-Green Group 146B.

*Length.*—Canes are about 27 cm from the base of the plant to the flowering portion.

*Diameter.*—About 7 mm.

*Internodes.*—On mature canes about 60 to 85 mm between nodes.

*Surface texture.*—Young wood: Smooth. Older wood: Smooth.

Long prickles:

*Incidence.*—9 prickles per 10 cm of stem.

*Size.*—Average length of prickles on mature stems is 6 mm.

*Shape.*—Upper portion is linear. Lower portion is concave.

*Color.*—Juvenile prickles: Greyed-Yellow Group 160B. Mature prickles: Greyed-Red Group 178C.

Plant foliage:

*Compound leaf.*—About 145 mm (l)×80 mm (w).

*Quantity.*—2 leaves per 10 cm of stem on average.

*Leaf bearing angle to the stem.*—45 degrees.

*Color of juvenile foliage.*—Upper side: Yellow-Green Group 144A with intonations of Greyed-Purple Group 183B at margins. Lower side: Yellow-Green Group 146D shaded with Greyed-Purple Group 183B.

*Color of mature foliage.*—Upper side: Yellow-Green Group 147A. Lower side: Yellow-Green Group 147B.

Plant leaves and leaflets:

*Stipules.*—Size: 16 mm long, 4 mm wide. Quantity: 2 per compound leaf. Shape: Linear, slightly broad based with outward extending apices. Margins: Finely serrated. Color: Yellow-Green Group 144A.

*Petiole.*—Length: 25 mm. Diameter: 2 mm. Upper surface color: Yellow-Green Group 146A. Lower surface color: Yellow-Green Group 144A.

*Rachis.*—Length: 51 mm. Upper surface color: Yellow-Green Group 146A. Lower surface color: Yellow-Green Group 144A.

*Leaflet.*—Quantity: Normally 5 leaflets, occasionally 3. Margins: Double serrate. Moderate undulations. Size: Terminal leaflets are about 66 mm long, 41 mm wide. Shape: Generally elliptical. Base: Rounded. Apex: Acute. Texture: Smooth on the upper surface, rugose on the lower surface. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren037' substantially as described and illustrated herein.

* * * * *

'Poulren037'

'Poulren037'